(12) United States Patent
Aker et al.

(10) Patent No.: US 9,834,524 B2
(45) Date of Patent: Dec. 5, 2017

(54) ISOXAZOLES, A PROCESS FOR THEIR PREPARATION AND USES THEREOF

(71) Applicant: Sanko Tekstil Isletmeleri San. Ve Tic. A.S., Inegol - Bursa (TR)

(72) Inventors: Acelya Aker, Esenler—Istanbul (TR); Nuket Ocal, Esenler—Istanbul (TR); Hikmet Nil Ergindemir, Esenler—Bursa (TR); Agamirze Hamitbeyli, Esenler—Bursa (TR)

(73) Assignee: SANKO TEKSTIL ISLETMELERI SAN. VE TIC. A.S., Inegol-Bursa (TR)

( * ) Notice: Subject to any disclaimer, the term of this patent is extended or adjusted under 35 U.S.C. 154(b) by 0 days.

(21) Appl. No.: 15/284,708

(22) Filed: Oct. 4, 2016

(65) Prior Publication Data

US 2017/0101385 A1 Apr. 13, 2017

(30) Foreign Application Priority Data

Oct. 7, 2015 (EP) .................................... 15188785

(51) Int. Cl.
C07D 261/14 (2006.01)
A01N 25/08 (2006.01)
A01N 43/80 (2006.01)
B65D 65/42 (2006.01)

(52) U.S. Cl.
CPC ........... *C07D 261/14* (2013.01); *A01N 25/08* (2013.01); *A01N 43/80* (2013.01); *B65D 65/42* (2013.01)

(58) Field of Classification Search
CPC ........ B65D 65/42; A01N 25/08; A01N 43/80; C07D 261/14
See application file for complete search history.

(56) References Cited

FOREIGN PATENT DOCUMENTS

WO WO2004/050644 A2 6/2004

OTHER PUBLICATIONS

European Search Report of EP priority application No. 15188785.8 dated Mar. 14, 2016.
Vikas Pandey et al:"Comparative study of conventional and microwave-assisted synethsis of some Schiff . . . ",Medicinal Chemistry Research.,vol. 21,No. 6, Feb. 17, 2011,pag844-852.

*Primary Examiner* — Mark V Stevens

(57) ABSTRACT

The present invention relates to novel isoxazoles, a process for their preparation and their use in the preparation of technical textiles and PPE's (Personal Protective Equipments), namely in the preparation of UV-protective and anti-infective textiles and garments.

15 Claims, 25 Drawing Sheets

$^1$H NMR Spectrum $^1$H NMR Spectrum

Figure 15
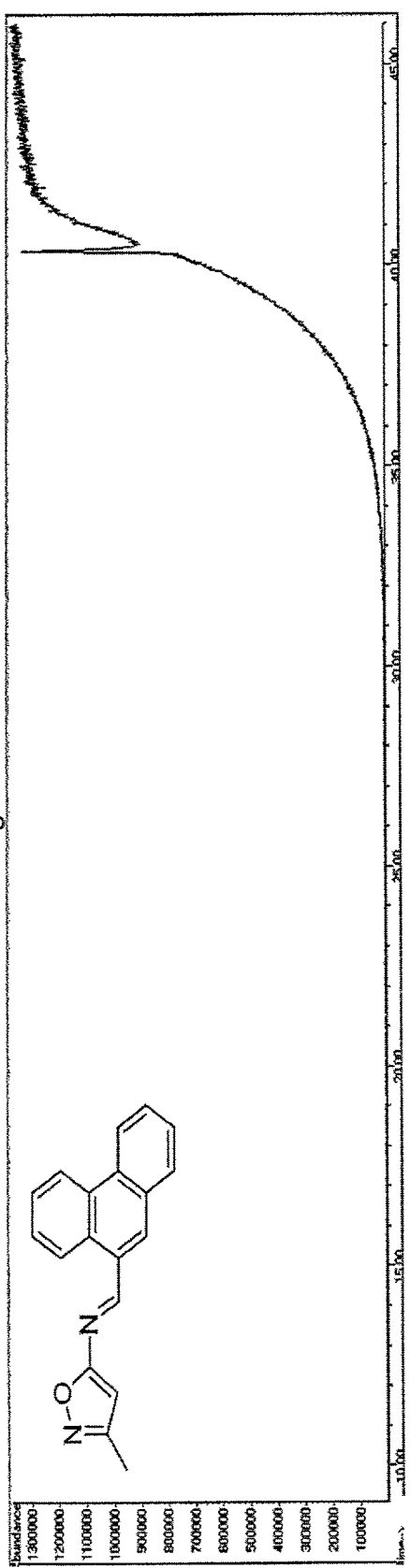
GC-MS Spectrum
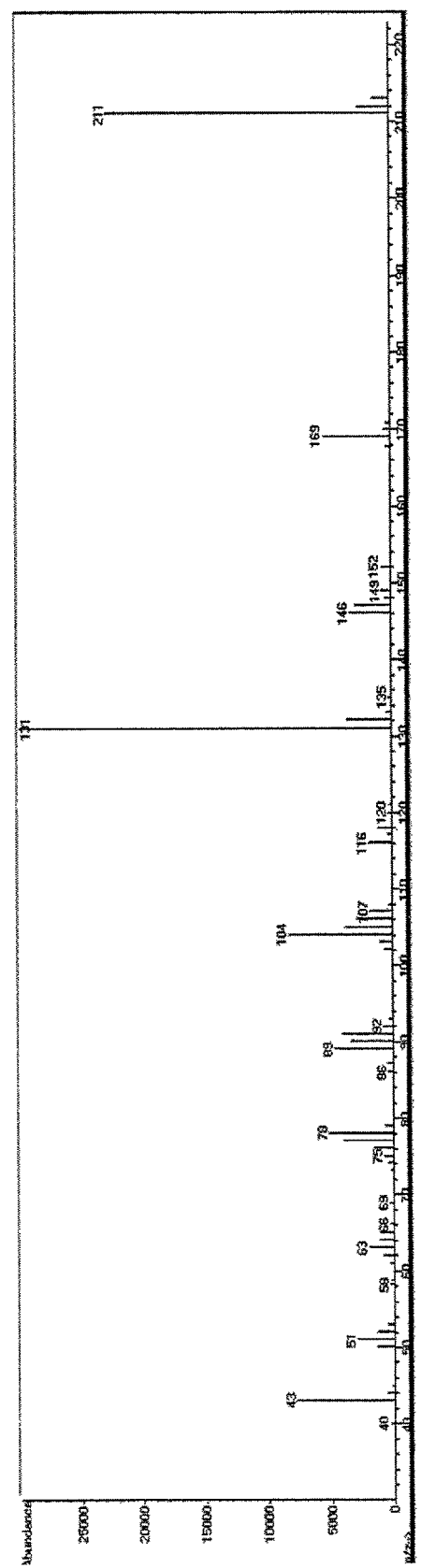

Figure 17

FTIR (ATR) Spectrum

¹³C NMR Spectrum

Figure 21

| Number of Specimen | UVA TRANSMITTANCE (315-400 nm) (%) | UVB TRANSMITTANCE (280-315 nm) | ULTRAVIOLET PROTECTION FACTOR (UPF) | UVA BLOCKING (%) | UVB BLOCKING (%) |
|---|---|---|---|---|---|
| 1 | 6.1 | 2.3 | 28.6 | 93.9 | 97.7 |
| 2 | 5.2 | 1.6 | 39.7 | 94.8 | 98.4 |
| 3 | 4.9 | 1.8 | 36.4 | 95.1 | 98.2 |
| 4 | 6.7 | 2.5 | 27.3 | 93.3 | 97.5 |
| 5 | 4.8 | 1.8 | 38.2 | 95.2 | 98.2 |
| 6 | 6.2 | 2.1 | 30.0 | 93.8 | 97.9 |
| AVERAGE | 5.65 | 2.02 | 33.37 | 94.35 | 97.98 |
| STANDARD DEVIATION | 0.79 | 0.34 | 5.36 | 0.79 | 0.34 |

ULTRAVIOLET PROTECTION VALUE for LABEL (According to ASTM D 6603- Unprepared Specimen): 27

Protection Classification

Good UV-protection category: between 15 and 24 UPF Value

Very Good UV-protection category: between 25 and 39 UPF Value

Excellent UV-protection category to UPF Value 40 or greater

Figure 22

| Number of Specimen | UVA TRANSMITTANCE (315-400 nm) (%) | UVB TRANSMITTANCE (280-315 nm) | ULTRAVIOLET PROTECTION FACTOR (UPF) | UVA BLOCKING (%) | UVB BLOCKING (%) |
|---|---|---|---|---|---|
| 1 | 0.1 | 0 | 1504.7 | 99.9 | 100.0 |
| 2 | 0.1 | 0.1 | 1310.7 | 99.9 | 99.9 |
| 3 | 0.5 | 0 | 1655.5 | 99.5 | 100.0 |
| 4 | 0.7 | 0 | 1617.9 | 99.3 | 100.0 |
| 5 | 0.2 | 0.1 | 2383.4 | 99.8 | 99.9 |
| 6 | 0 | 0.1 | 1783.0 | 100.0 | 99.9 |
| AVERAGE | 0.27 | 0.05 | 1709.2 | 99.73 | 99.5 |
| STANDARD DEVIATION | 0.27 | 0.05 | 366.56 | 0.27 | 0.05 |

ULTRAVIOLET PROTECTION VALUE for LABEL (According to ASTM D 6603- Unprepared Specimen): 1324
Protection classification: Excellent UV protection Category to UPF value 40 or greater Protection Classification Good UV-protection category : between 15 and 24 UPF Value Very Good UV-protection category: between 25 and 39 UPF Value Excellent UV-protection category to UPF Value 40 or greater.

Figure 23

DRY

| Number of Specimen | UVA TRANSMITTANCE (315-400 nm) | UVB TRANSMITTANCE (280-315 nm) | ULTRAVIOLET PROTECTION FACTOR (UPF) | UVA blocking (%) | UVB blocking (%) |
|---|---|---|---|---|---|
| 1 | 2.8 | 0.1 | 196.8 | 97.2 | 99.9 |
| 2 | 3.4 | 0.1 | 254.3 | 96.6 | 99.9 |
| 3 | 2.8 | 0.2 | 195.9 | 97.2 | 99.8 |
| 4 | 2.3 | 0.2 | 232.7 | 97.7 | 99.8 |
| 5 | 2.5 | 0.1 | 228.7 | 97.5 | 99.9 |
| 6 | 2.5 | 0.2 | 232.7 | 97.5 | 99.8 |
| AVERAGE: | 2.72 | 0.15 | 223.52 | 97.28 | 99.85 |
| STANDARD DEVIATION: | 0.39 | 0.05 | 22.89 | 0.39 | 0.05 |
| * ULTRAVIOLET PROTECTION FACTOR FOR LABEL | | | +40 | | |

Protection Classification

Good UV-protection category : between 15 and 24 UPF Value

Very Good UV-protection category: between 25 and 39 UPF Value

Excellent UV-protection category to UPF Value 40 or greater

Figure 24

| Number of Specimen | UVA TRANSMITTANCE (315-400 nm) (%) | UVB TRANSMITTANCE (280-315 nm) (%) | ULTRAVIOLET PROTECTION FACTOR (UPF) | UVA BLOCKING(%) | UVB BLOCKING(%) |
|---|---|---|---|---|---|
| 1. | 2.9 | 0.1 | 231.6 | 97.1 | 99.9 |
| 2. | 3.4 | 0.1 | 278.3 | 96.6 | 99.9 |
| 3. | 2.8 | 0.1 | 359.1 | 97.2 | 99.9 |
| 4. | 2.8 | 0 | 310.3 | 97.2 | 100.0 |
| 5. | 2.8 | 0 | 321.0 | 97.2 | 100.0 |
| 6. | 2.9 | 0 | 345.3 | 97.1 | 100.0 |
| Average: | 2.93 | 0.05 | 307.6 | 97.07 | 99.95 |
| Standard Deviation: | 0.23 | 0.05 | 46.68 | 0.23 | 0.05 |

UPF= 50+(258)

Protection Classification

Good UV-protection category: between 15 and 24 UPF Value

Very Good UV-protection category: between 25 and 39 UPF Value

Excellent UV-protection category to UPF Value 40 or greater

Figure 25

| Number of Specimen | UVA TRANSMITTANCE (315-400 nm) (%) | UVB TRANSMITTANCE (280-315 nm) (%) | ULTRAVIOLET PROTECTION FACTOR (UPF) | UVA BLOCKING(%) | UVB BLOCKING(%) |
|---|---|---|---|---|---|
| 1. | 0.1 | 0.1 | 432.5 | 99.9 | 99.9 |
| 2. | 0.2 | 0.2 | 284.4 | 99.8 | 99.8 |
| 3. | 0.3 | 0.1 | 739.2 | 99.7 | 99.9 |
| 4. | 0.6 | 0.2 | 229.4 | 99.4 | 99.8 |
| 5. | 0.3 | 0.1 | 619.4 | 99.7 | 99.9 |
| 6. | 0.1 | 0.1 | 886.2 | 99.9 | 99.9 |
| Average: | 0.27 | 0.13 | 531.89 | 99.73 | 99.87 |
| Standard Deviation: | 0.19 | 0.05 | 260.31 | 0.19 | 0.05 |

UPF= 50+(258)

Protection Classification

Good UV-protection category: between 15 and 24 UPF Value

Very Good UV-protection category: between 25 and 39 UPF Value

Excellent UV-protection category to UPF Value 40 or greater

ISOXAZOLES, A PROCESS FOR THEIR PREPARATION AND USES THEREOF

RELATED APPLICATION

This application is related to and claims priority to European application No. EP 15188785.8 filed Oct. 7, 2015, the contents of which are hereby incorporated by reference as if set forth in their entirety.

BACKGROUND

Ultraviolet radiation (both UVA and UVB) contributes to sunburn, skin aging, eye damage and skin cancer. It is therefore commonly acknowledged the importance to avoid excessive exposure to the sun and to protect by applying sunscreens to the skin.

Recently sun-protecting clothing is becoming popular, said clothing being called PPEs (Personal Protective Equipment). In some cases, PPEs are also able to protect the body from infections, creating a barrier between the wearer and germs and are especially useful for health-care or biological laboratory workers. Indeed, PPEs are designed to reduce the exposure to hazards, either being them caused by sun or other UV source exposure or by bacteria, fungi, virus and the like.

There is a need to develop improved fabrics for the manufacture of PPEs which provide a more effective barrier between the wearer and the environment.

BRIEF DESCRIPTION OF THE DRAWINGS

FIGS. 1 to 20 show the analytical data of the compounds of the examples.

FIGS. 21 to 25 show the results of the UPF test on a non-treated and on treated fabrics.

DETAILED DESCRIPTION

Figure 1:
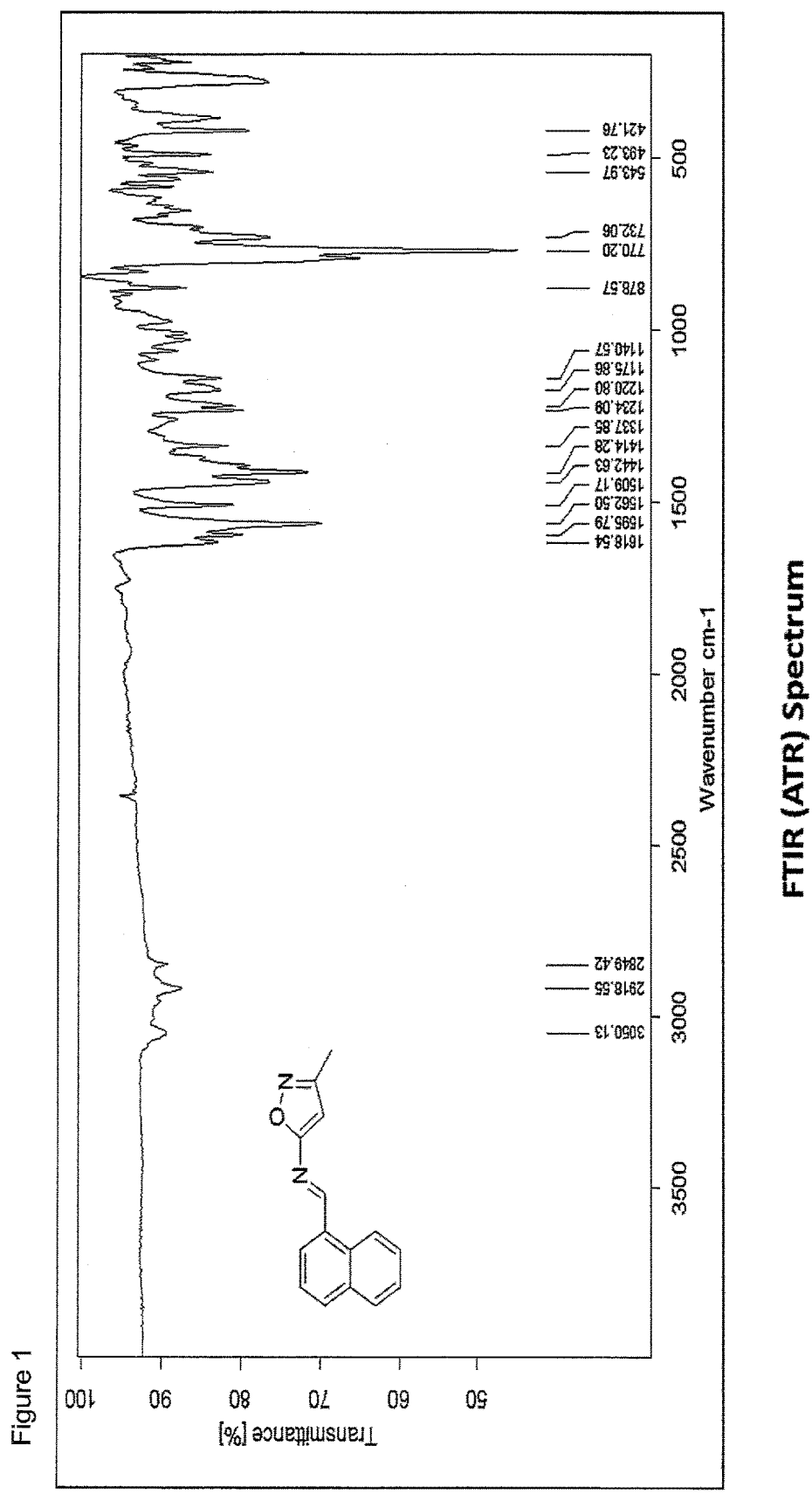

It is a scope of the invention to provide new compounds bearing an isoxazole ring.

It is a further scope of the invention to provide new compounds which are able to impart a textile sun-protective and anti-infective effect. It is a further scope of the invention to provide garments and PPEs which are endowed with sun-protective and anti-infective effect and which are made from the new compounds of the invention. It is another scope of the invention to provide a process for the preparation of the new compounds of the invention.

These and further scopes will be achieved by the subject-matter of the invention, as it will be herein disclosed.

According to one of its aspects, the present invention relates to new compounds of formula (I)

(I)

wherein
$R_1$ is a non-substituted aromatic fused polycyclic hydrocarbon having 10 to 18 carbon atoms;

$R_2$ is a non-substituted, saturated or unsaturated, linear or branched, acyclic C1-C10 alkyl group.

According to a preferred embodiment, $R_1$ is a group selected from naphthalenyl, anthracenyl and pyrenyl. Particularly preferred are 1-naphthalenyl; 2-naphthalenyl; 9-anthracenyl and 1-pyrenyl groups.

According to a preferred embodiment, $R_2$ is a C1-C4 alkyl group, more preferably a methyl group.

In compounds of formula (I), due to the emplacement on isoxasole ring, syn-anti geometric isomerism may be present. All the possible geometric isomers are encompassed by the present invention.

The compounds of the invention may be prepared by a process according to the following Scheme (II)  (III)

(I)

The above depicted process represents another subject-matter of the invention.

In the process of the invention, a compound of formula (II) is reacted with the carboxylic aldehyde of formula (III) in an appropriate solvent, with an acid catalyst. Compounds of formula (II) and (III) are known in the art or can be prepared by known methods.

Preferably the molar ratio compound (II)/compound (III) is approx. 1/1. Preferred solvents are selected from aromatic solvents, such as toluene and lower alcohols, such as ethanol. However, any solvent showing a polarity similar to that of the preferred solvents may be used, according to the present invention.

To achieve the acid catalyst, it is possible to add catalytic amounts of BrØsted acids to the reaction mixture, preferably a strong organic acid, such as p-toluenesulfonic acid (TsOH).

The reaction is advantageously carried out at a temperature between the 50° C. and the reflux temperature of the reaction mixture, the reflux temperature being preferred.

It is also preferred to add absorbent agents to the reaction mixture for increasing the efficiency, such as silica or alumina and molecular sieves for remove occurring water. It is also advantageous to perform the reaction in an inert environment, such as nitrogen or argon atmosphere.

The reaction is generally completed in a few hours such as, for instance, 2 to 6 hours. The skilled in the art is however able to follow the development of the reaction flow and finishing time, which can be determined, for instance, by using TLC (Thin Layer Chromatography) technique.

As an alternative to conventional heating, the reaction mixture may be irradiated with microwaves, preferably with low potency microwaves such as 300-400 W for a few minutes.

Upon completion of the reaction, compound of formula (I) is generally isolated by filtration and, advantageously, purified according to the conventional methods such as, for instance, stirring with one or more solvents and filtering or by chromatographic techniques.

Detailed examples of the above reaction are provided in the experimental section of the present description.

Compounds of formula (I) may be used to impart sun-protective and anti-infective effect to textiles. The expressions "sun-protective effect" means that the textile and the garments made therewith are able to protect the wearer from UV radiation. The expression "anti-infective effect" means that the textile and the garments are able to protect the body from infections, creating a inhibition area and destroys the germs, such as bacteria, especially Gram (+) bacteria and/or fungi and/or virus and/or protozoa and/or helminths.

Indeed, it was found out that coating fabrics with the compounds of the invention increases the UPF (Ultraviolet Protection Factor) label values and, also, confers to the fabric anti-microbial effects, especially anti-bacterial effects, particularly Gram (+) bacteria. This is a valuable technical outcome that allows the treated fabrics to be used in the manufacture of, i.a. PPEs.

The use of compounds of formula (I) in the textile field, in the preparation of sun-protective and anti-infective fabrics and in the manufacture of PPEs is also a subject-matter of the invention, as well as fabrics, clothing and PPEs treated, especially coated, with the compounds of formula (I).

It is another subject-matter of the invention a method to make fabrics sun-protective and anti-infective fabrics which comprises treating said fabrics with the compounds of formula (I).

The terms "treat" or "treating" mean that fabrics or clothing or the like are coated or soaked with the compound of the invention.

These fabrics may be obtained by dissolving the compounds of the invention in a suitable solvent, i.e in a solvent which is able to dissolve compounds of formula (I), such as for instance dichloromethane, and the solution may be added in to a conventional printing paste and then applied to the fabrics.

The flat bed screen method for printing application may be carried out, wherein acrylic and modified polymeric resins, as well as conventional cross-linkers may be used for printing paste. The fabrics may then preferably be cured, for instance at 130° C. for 3-5 minutes.

Any kind of fabrics can be coated with the compounds of the invention, including woven, knotted and non-woven fabrics. Preferably, the fabrics are cotton fabrics, advantageously a 100% cotton fabrics. The fabrics may also be denim.

In order to determine if the UV radiation blocked or transmitted by textile fabrics, the known method AATCC 183 was followed. Details of the method are given in the experimental section of the description.

As it can be seen in the experimental section, fabrics treated with the compounds of the invention showed surprisingly exceptional UPFs, all of them being well above the UPF value limit to be included in the "Excellent UV-protection category", i.e. UPF 40.

In order to determine if the antimicrobic activity of the textile fabrics, Washing Standart: BS EN ISO 6330 5A and Antibacterial Test Standart: AATCC 147:2011 were followed. Details of the method are given in the experimental section of the description.

EXPERIMENTAL SECTION

Example 1

3-methyl-N-(1-naphthalenylmethylen)-5-isoxazolamine

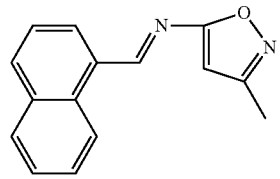 [SMILES: Cc1cc(/N=C/c2cccc3ccccc23)on1]

5-amino-3-methylisoxazole and 1-naphthalenylaldehyde in a molar ratio 1/1 are dissolved in absolute toluene in the presence of a catalytic amount of TsOH and molecular sieve and stirred at 110° C., under nitrogen atmosphere for 4 hours. The precipitate is the filtered, treated with acetonitrile and sonicated in an ultrasonic bath for 3 minutes. The solid is filtered and dried in oven to yield the compound of the title as yellow crystals (58% yield).

Figure 2:
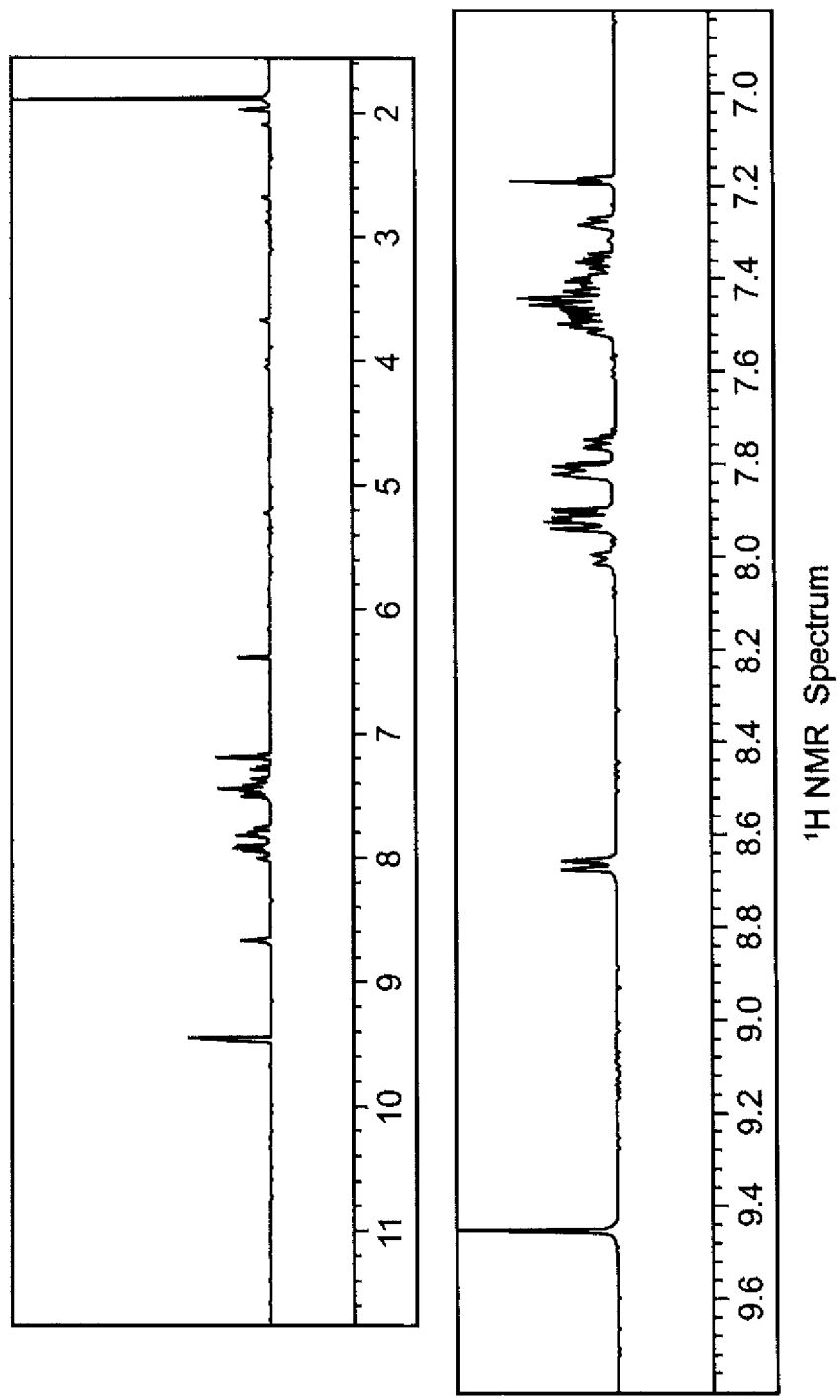
Figure 3:
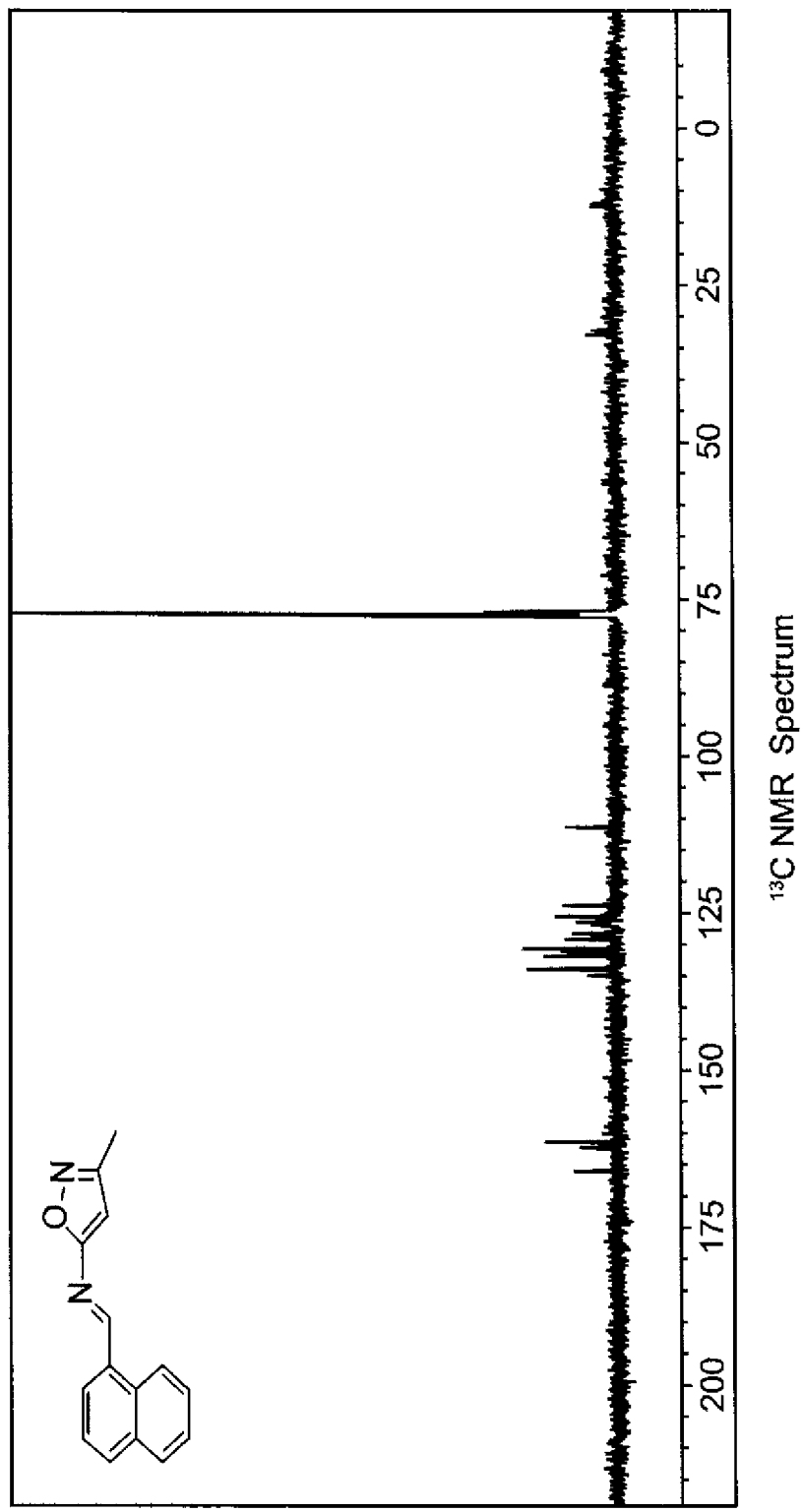
Figure 4:
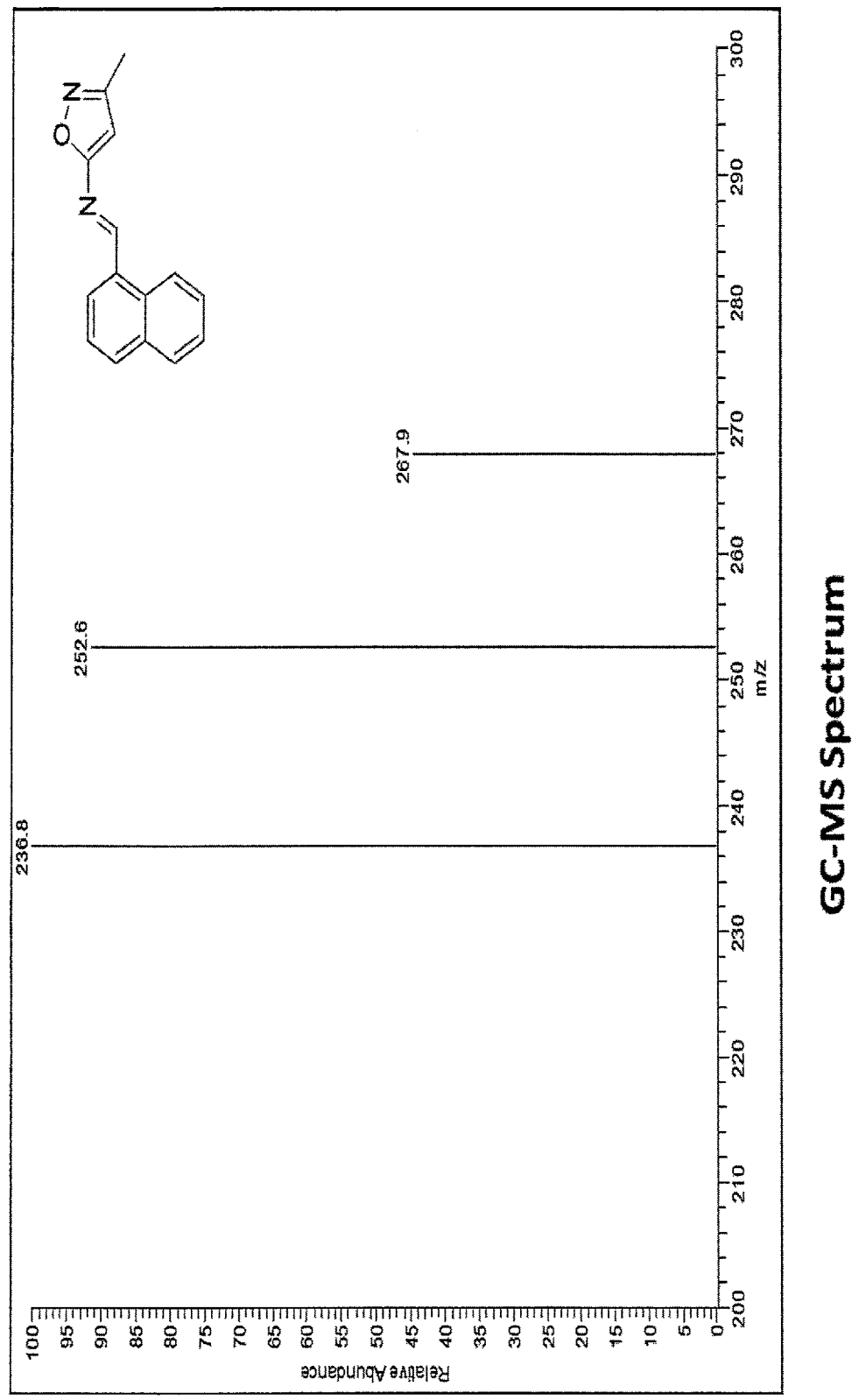
Figure 5:
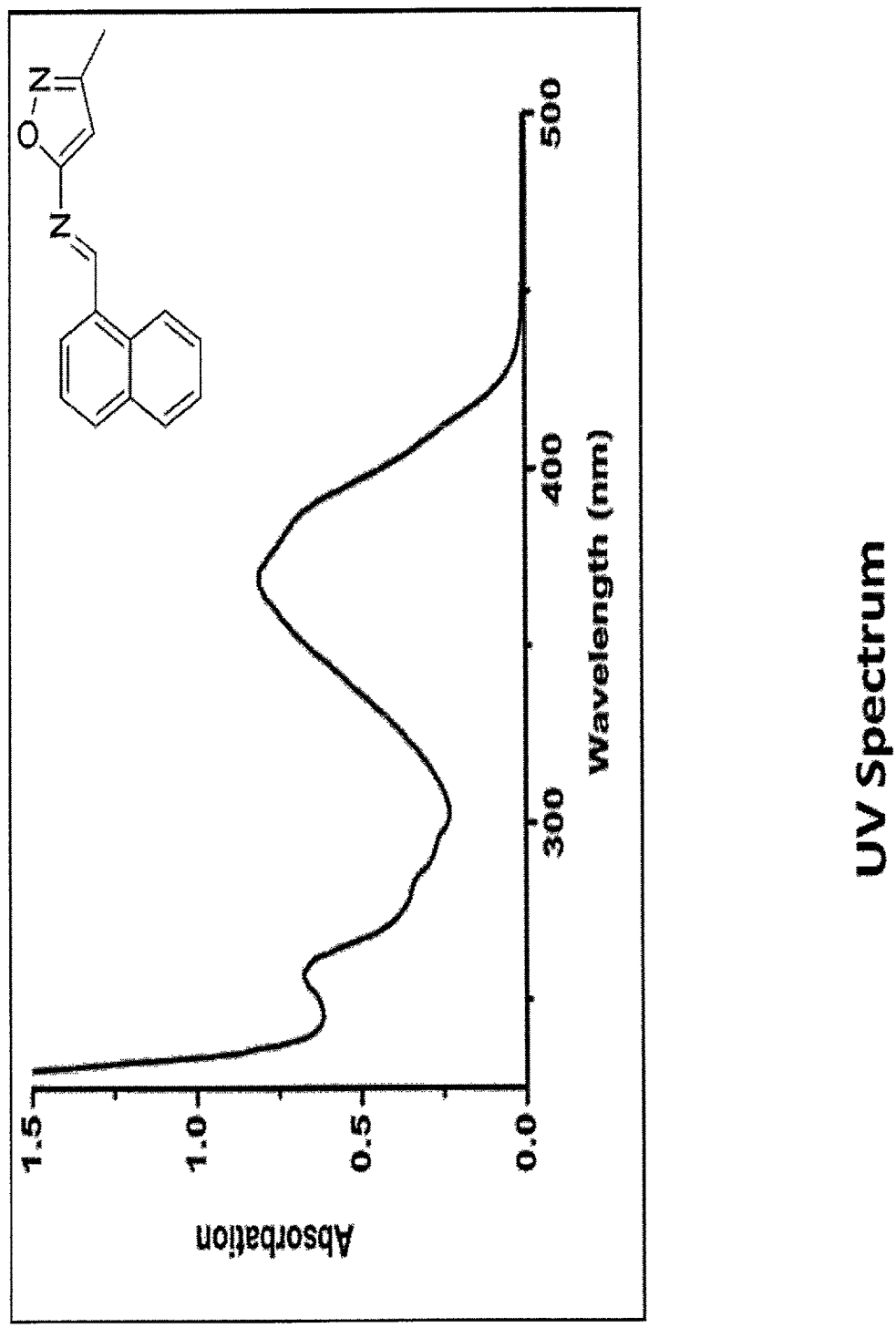

See FIGS. 1 to 5.

m.p.=90-92° C.; $R_f$=0.28 (1:5, ethyl acetate/n-hexane).

FTIR (ATR): ν=3050 (aromatic, =CH streching), 2918 ve 2849 (aliphatic, CH streching), 1618, 1595 and 1562 (C=C and C=N streching), 1442, 1414 (aliphatic, intraplanar CH bending), 1337 (methyl, intraplanar CH bending), 1175 (C—N swing), 732 ve 693 (monoaromatic, CH bending) $cm^{-1}$.

$^1$H NMR (CDCl$_3$, 500 MHz): δ=1.88 (s, 3H, CH$_3$), 6.38 (s, 1H, =CH), 7.34-7.51(m, 4H, aromatic), 7.81 (d, J=8.51 Hz, 1H, aromatic), 7.92 (dd, J=8.19; 11.65 Hz, 1H, aromatic), 8.66 (d, J=8.51 Hz, 1H, aromatic), 9.45 (s, 1H, =CH) ppm.

$^{13}$C NMR (CDCl$_3$, 125 MHz): δ=12.35 (CH$_3$), 111.19 (CH), 123.57 (CH), 125.28 (CH), 126.34 (CH), 127.89 (CH), 128.82 (CH), 130.51 (CH), 130.87 (CH), 131.70 (Cq), 133.42 (Cq), 133.62 (Cq), 161.21 (Cq), 162.23 (Cq), 165.82 (CH) ppm.

LC-MS: 236 (M$^+$).

UV (λmax, CH$_2$Cl$_2$): 385 nm (c=1.5×10$^{-4}$, A=0.80, ε=5.4×10$^3$)

Example 2

3-methyl-N-(2-naphthalenylmethylen)-5-isoxazolamine

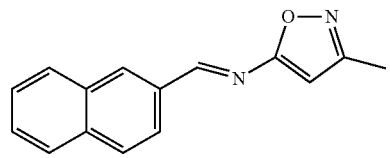 [SMILES: Cc1cc(/N=C/c2ccc3ccccc3c2)on1]

5-amino-3-methylisoxazole and 2-naphthalenylaldehyde in a molar ratio 1/1 are dissolved in absolute toluene in the presence of a catalytic amount of TsOH and molecular sieve and stirred at 110° C., under N$_2$ atmosphere for 4 hours. The precipitate is the filtered, treated with absolute ethanol and sonicated in an ultrasonic bath for 3 minutes. The solid is filtered and dried in oven to yield the compound of the title as yellow crystals (54% yield).

Figure 6:
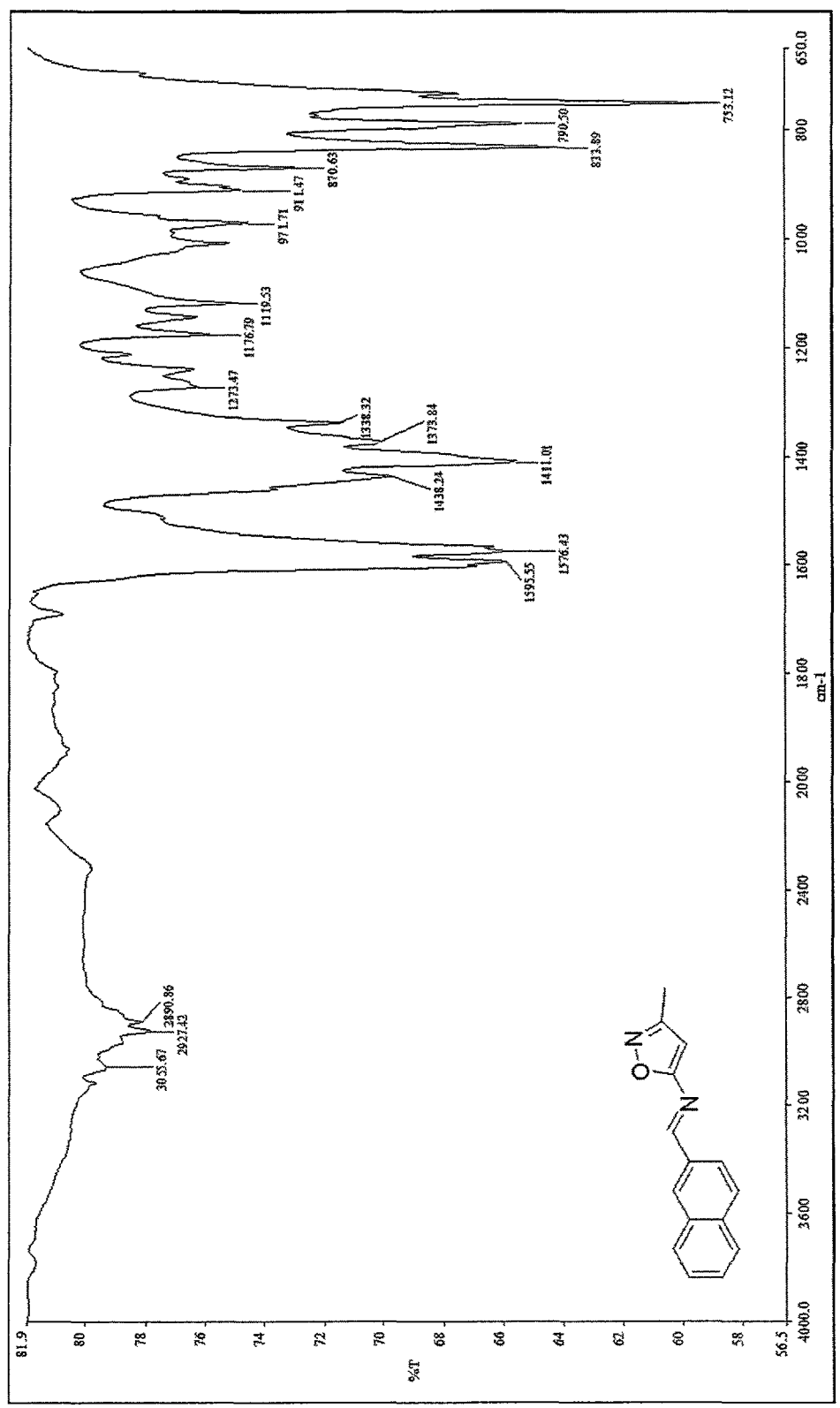
Figure 7:
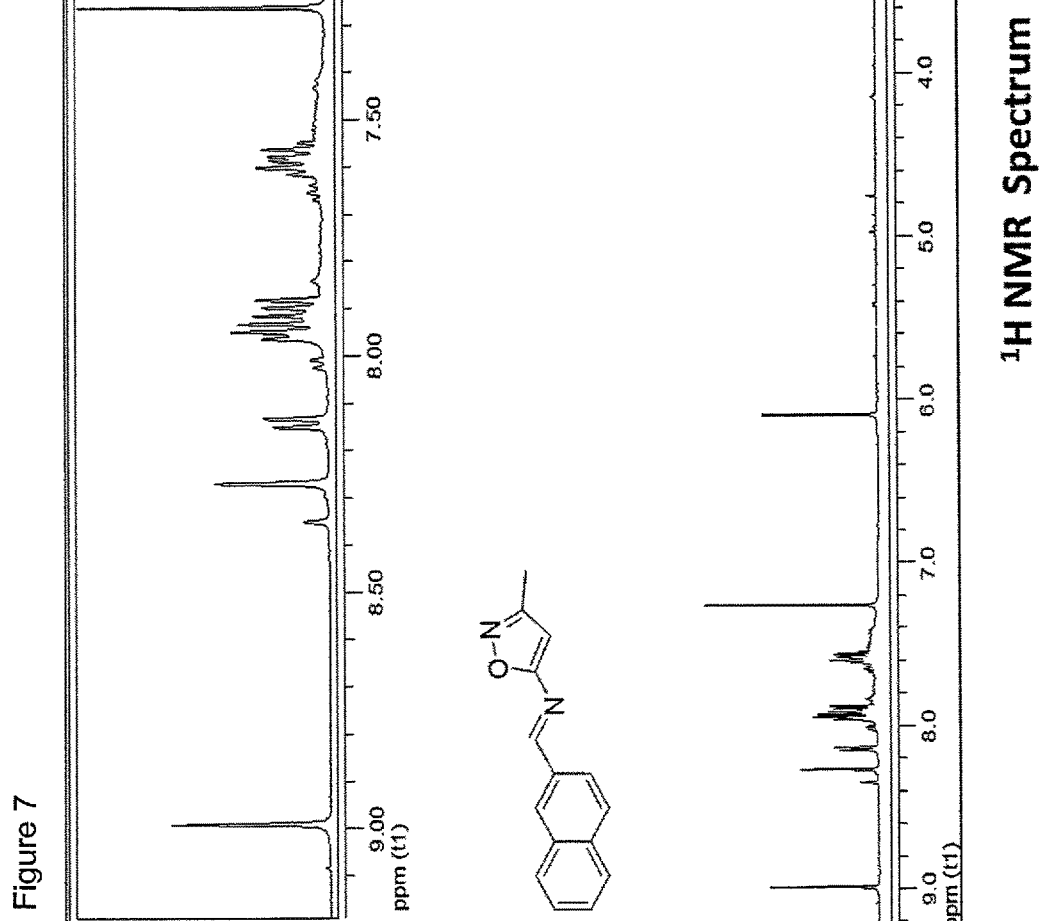
Figure 8:
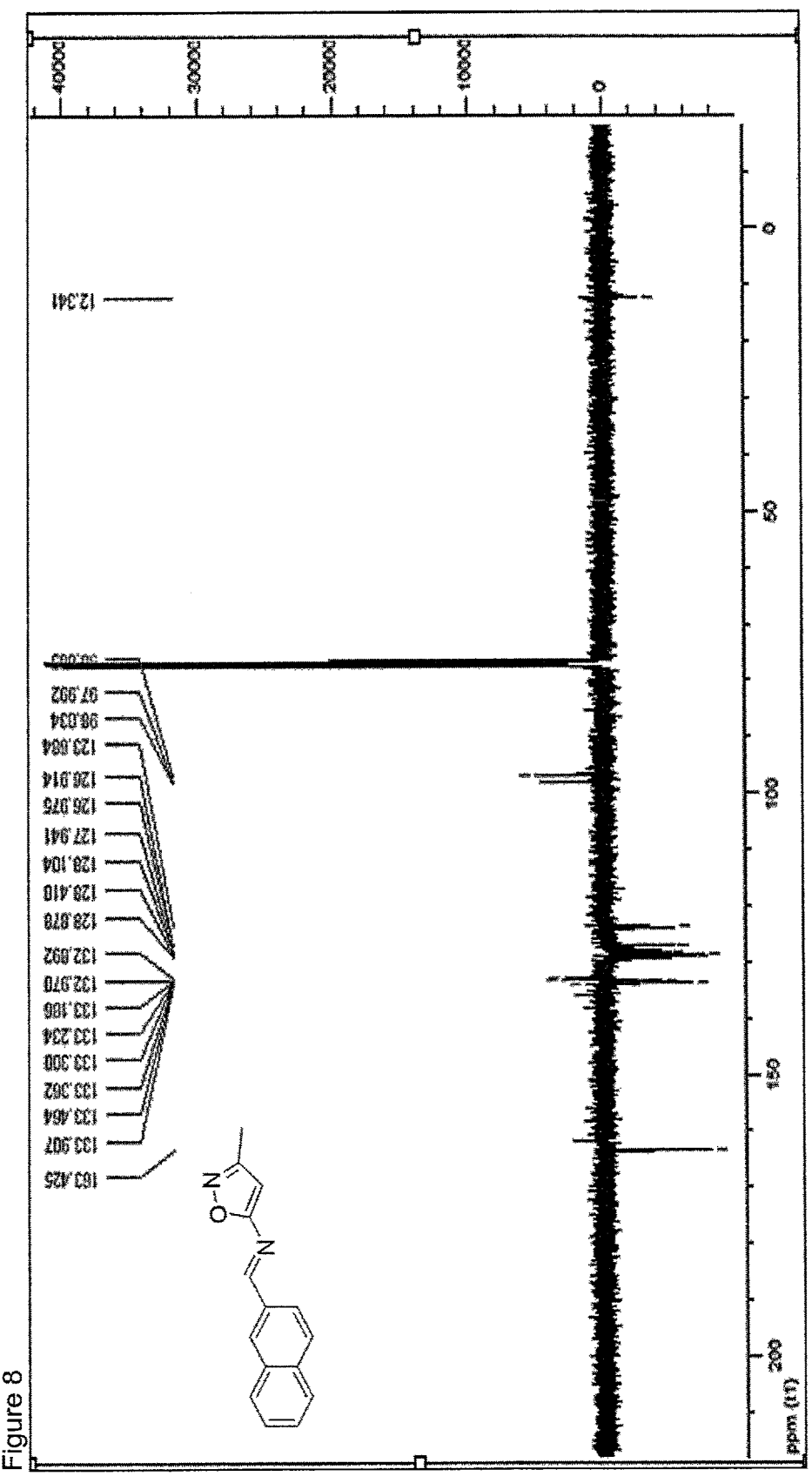
Figure 9:
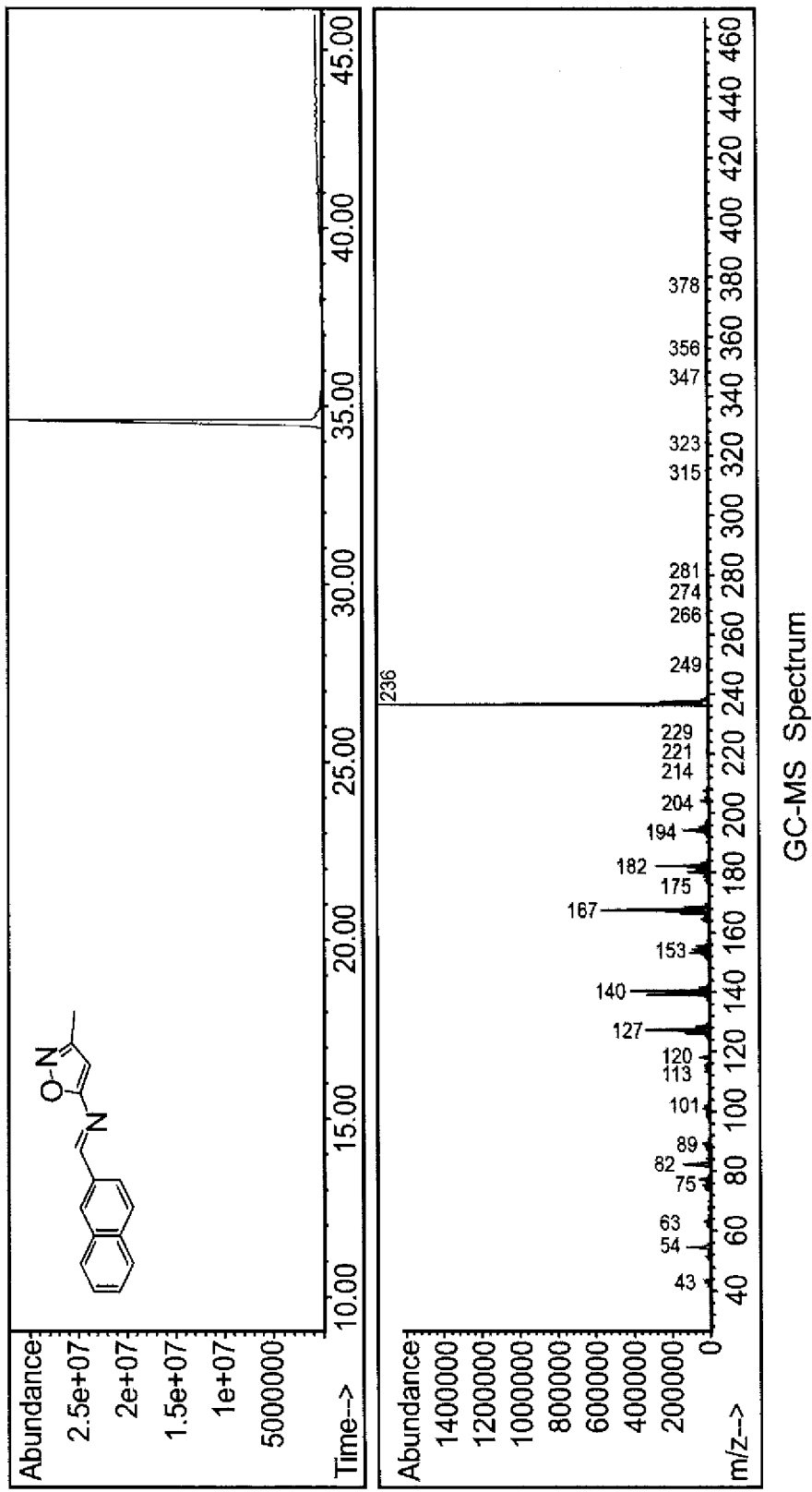
Figure 10:
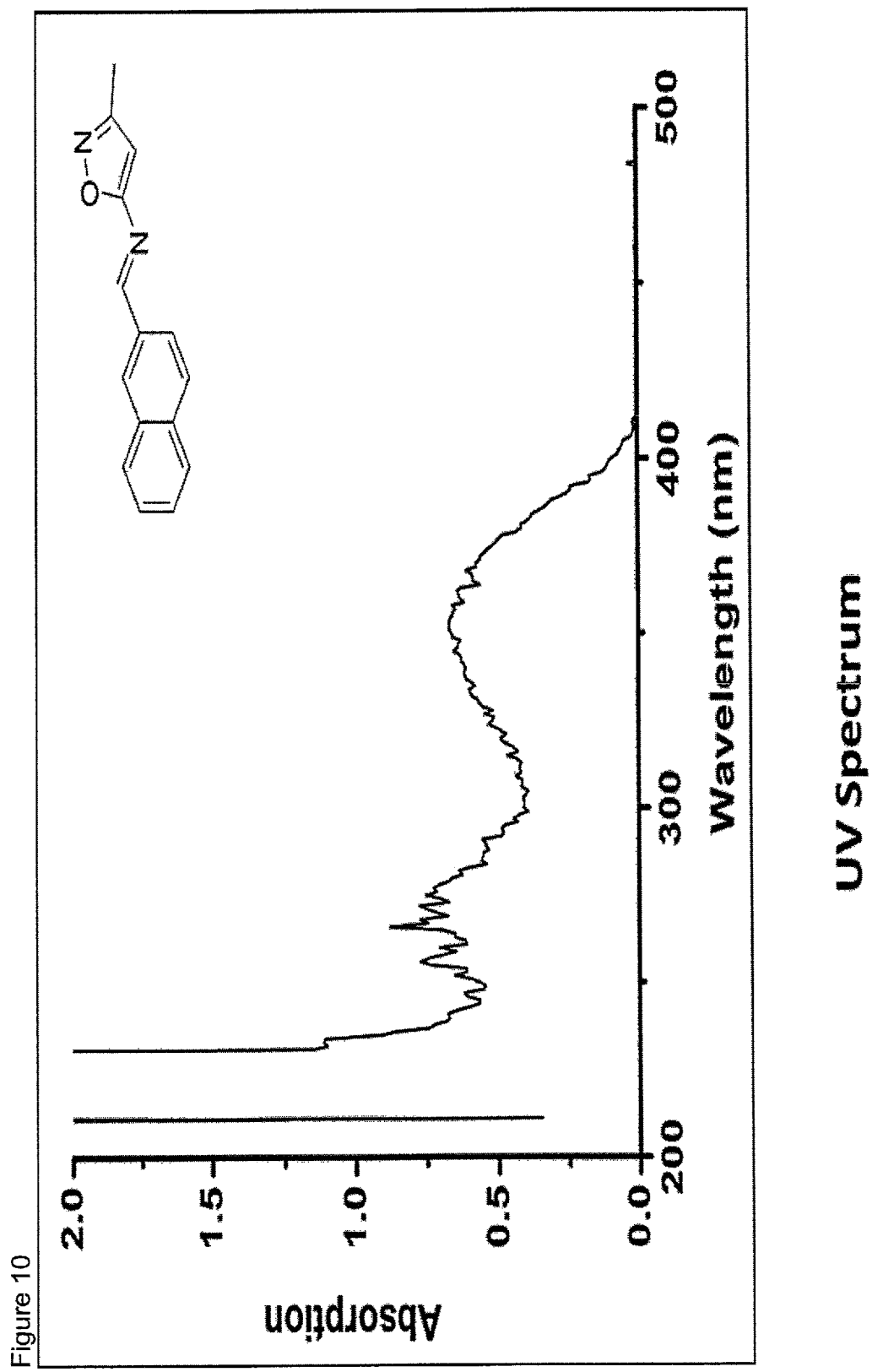

See FIGS. 6 to 10.

Yellow crystals; m.p.=195-197° C.; $R_f$=0.31 (1:5, ethyl acetate/n-hexane).

FTIR (ATR): ν=3055 (aromatic, =CH streching), 2927 ve 2890 (aliphatic, CH streching), 1595 and 1576 (C=C and C=N streching), 1438, 1411 (aliphatic, intraplanar CH bending), 1373 (methyl, intraplanar CH bending), 1176 (C—N swing), 753 ve 693 (monoaromatic, CH bending) cm$^{-1}$.

$^1$H NMR (CDCl$_3$, 500 MHz): δ=2.34 (s, 3H, CH$_3$), 6.01 (s, 1H, =CH), 7.54-7.61 (m, 2H, aromatic), 7.88-7.96 (m, 3H, aromatic), 8.14 (d, J=9.77 Hz, 1H, aromatic), 8.26 (s, 1H, aromatic), 8.99 (s, 1H, =CH) ppm.

$^{13}$C NMR (CDCl$_3$, 125 MHz): δ=12.33 (CH$_3$), 96.66 (CH), 123.68 (CH), 126.97 (CH), 127.93 (CH), 128.44 (CH), 128.87 (CH), 129.03 (CH), 132.97 (Cq), 133.36 (Cq), 135.70 (Cq), 138.17 (Cq), 161.66 (Cq), 163.42 (CH) ppm.

GC-MS: 236 (M$^+$).

UV (λmax, CH$_2$Cl$_2$): 350 nm (c=1.7×10$^{-7}$, A=0.875, ε=5.16×10$^6$)

Example 3

3-methyl-N-(9-phenanthrenylmethylen)-5-isoxazolamine

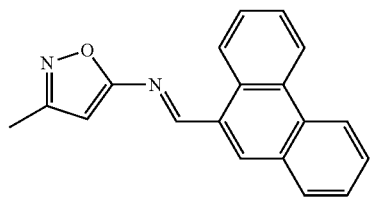 [SMILES: Cc1cc(/N=C/c2cc3ccccc3c3ccccc23)on1]

5-amino-3-methylisoxazole and 2-phenantrenylaldehyde in a molar ratio 1/1 are dissolved in absolute ethanol refluxed for 20 hours in the presence of molecular sieve. The liquid phase is evaporated and purified by column chromatography using silica gel as solid phase purified by column chromatography using silica gel as solid phase and 1/5: ethyl acetate/n-hexane eluent system to yield the compound of the title as yellow crystals (yield 42%).

Figure 11:
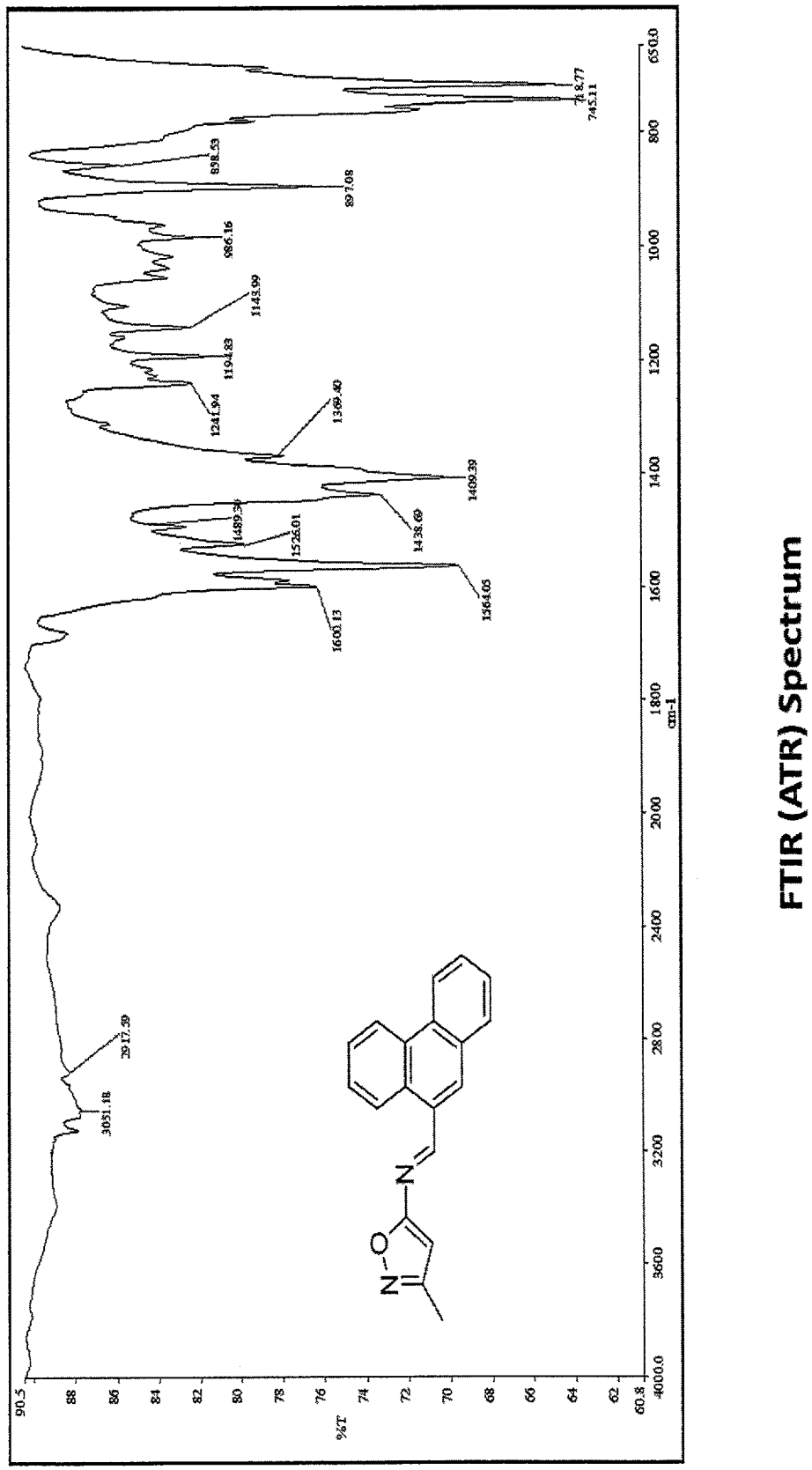
Figure 12:
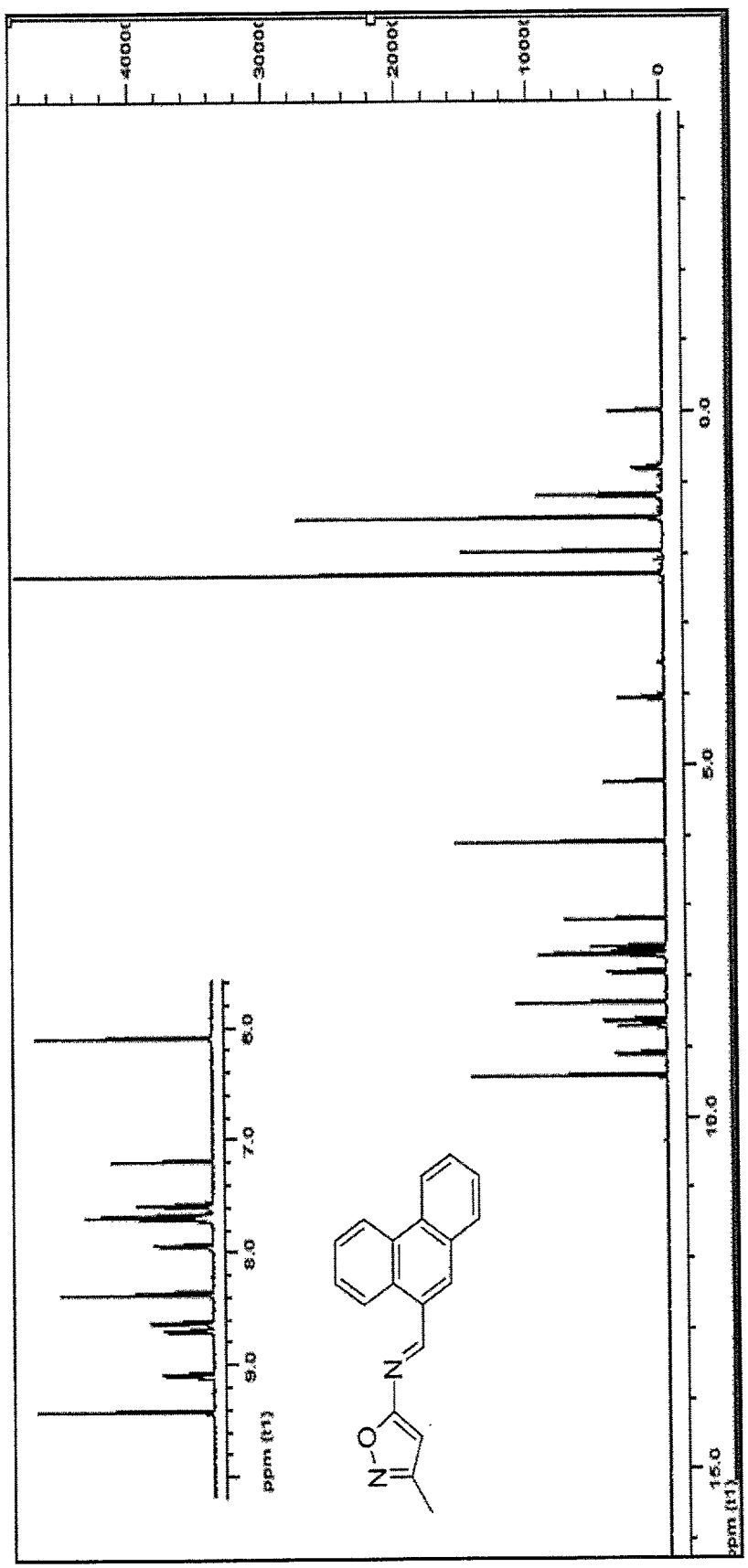
Figure 13:
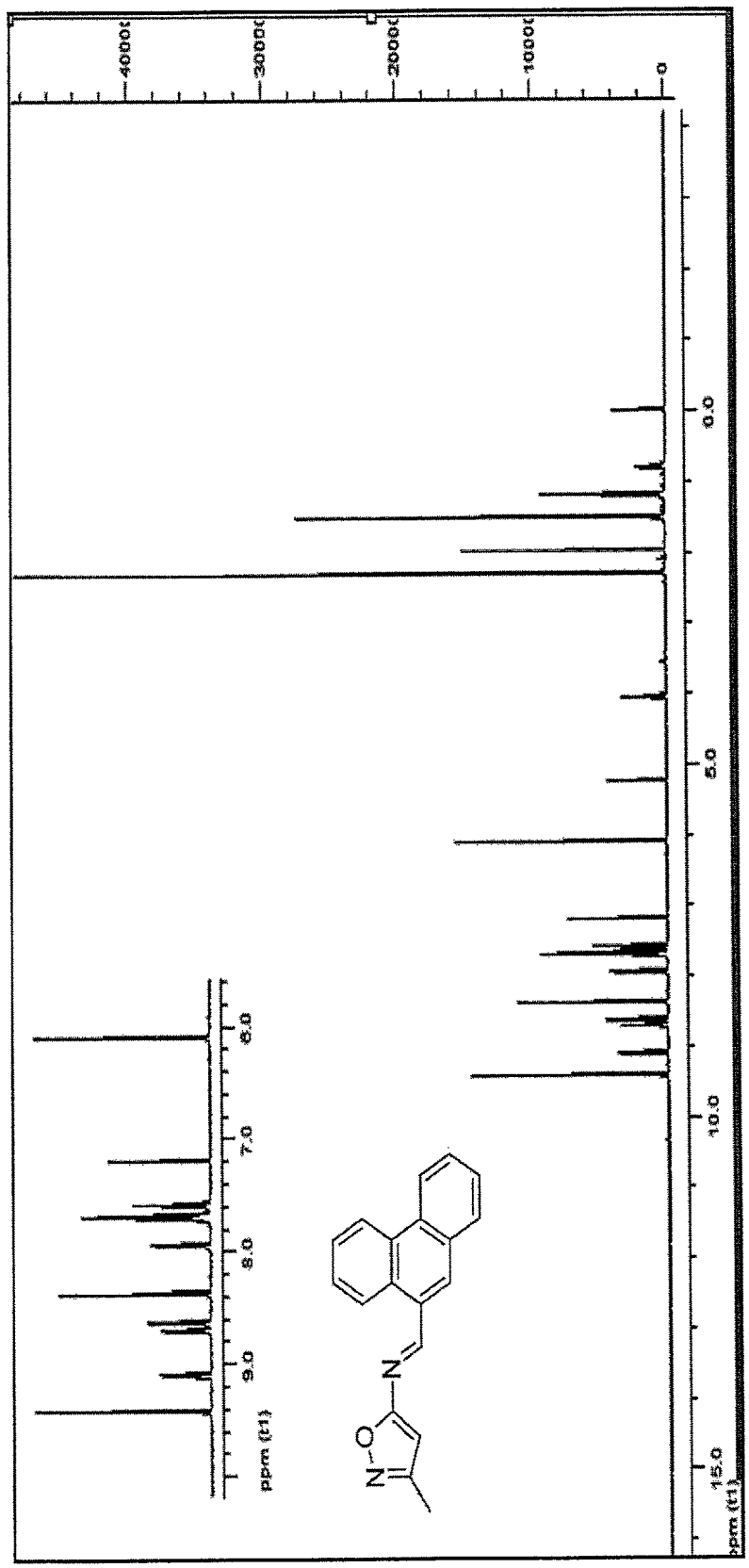
Figure 14:
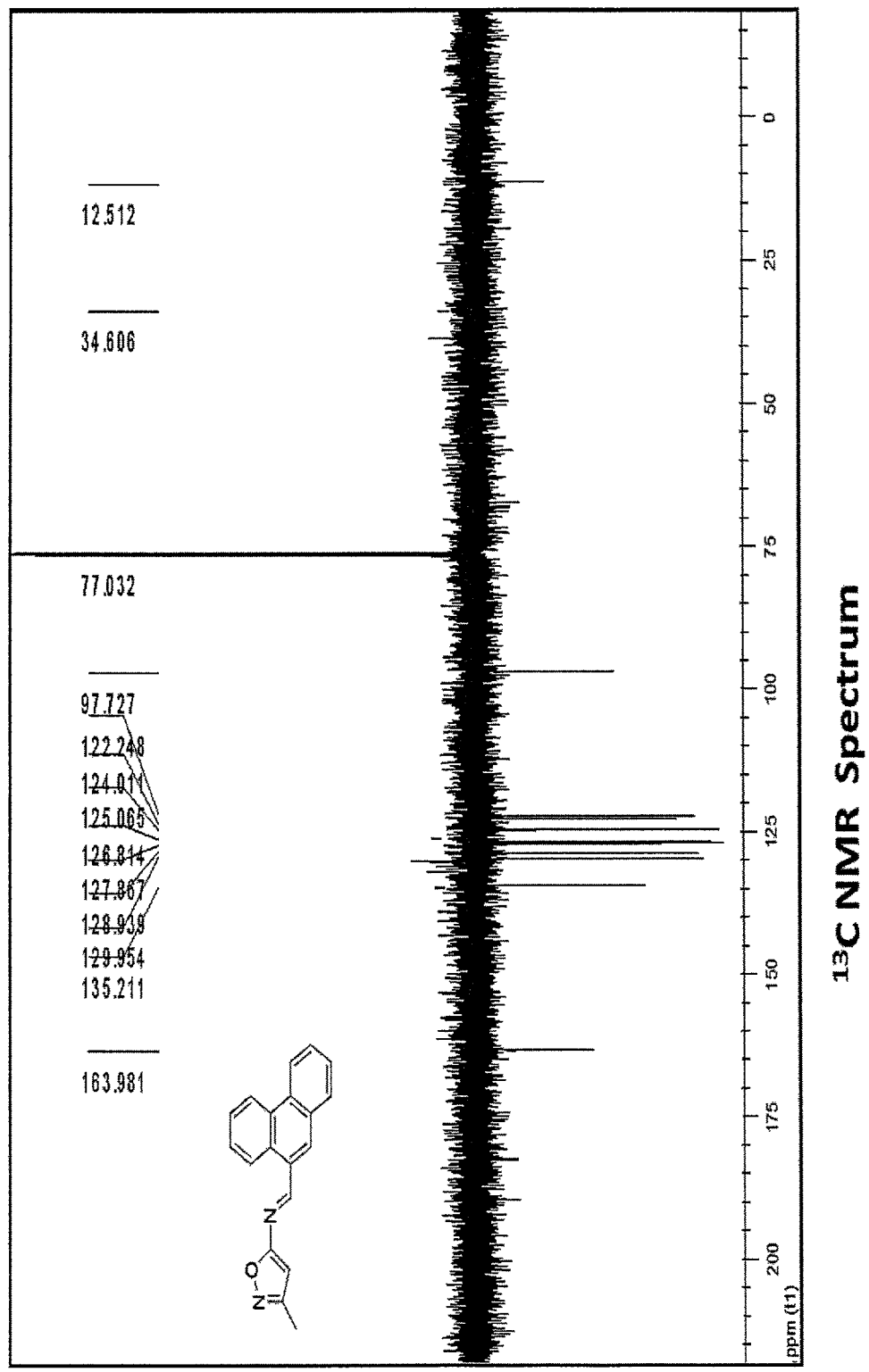
Figure 16:
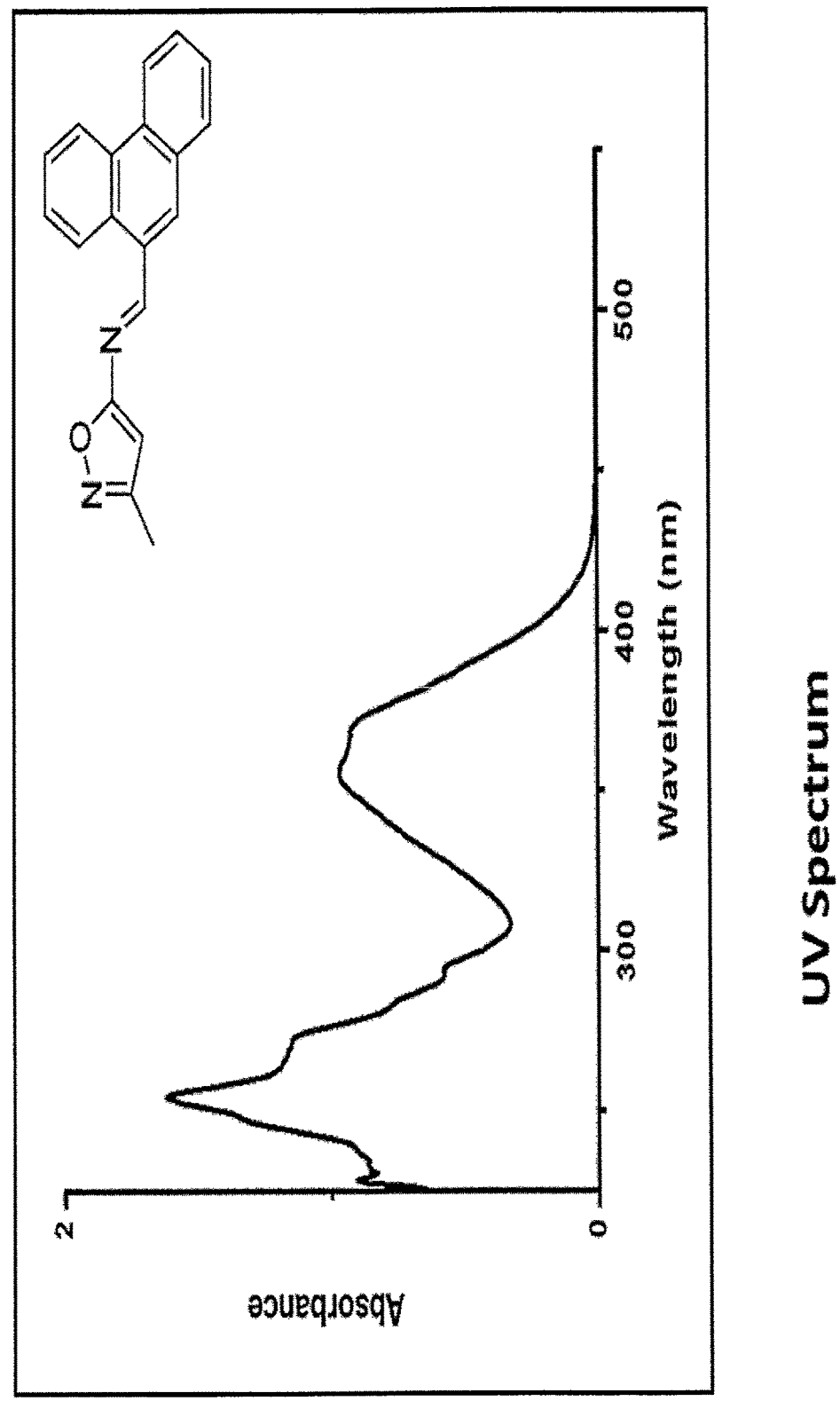

See FIGS. 11 to 16.

m.p.=170-171° C.; $R_f$=0.28 (1:5, ethyl acetate/n-hexane).

FTIR (ATR): ∟=3051 (aromatic, =CH streching), 2917 (aliphatic, CH streching), 1600 and 1564 (C=C and C=N streching), 1526, 1489, 1438, 1409 ve 1369 (aliphatic, intraplanar CH bending), 1194 (C—N swing), 745 ve 711 (monosubstitued aromatic ring, CH bending) cm$^{-1}$.

$^1$H NMR (CDCl3, 500 MHz): δ=2.30 (s, 3H, CH3), 6.09 (s, 1H, =CH), 7.57-7.60 (m, 1H, aromatic), 7.67-7.72 (m, 3H, aromatic), 7.95 (d, J=7.88 Hz, 1H, aromatic), 8.37 (s, 1H, aromatic), 8.63 (d, J=8.19 Hz, 1H, aromatic), 8.69-8.71 (m, 1H, aromatic), 9.09-9.11 (m, 1H, aromatic, 9.42 (s, 1H, =CH) ppm.

$^{13}$C NMR (CDCl3, 125 MHz): δ=12.20 (CH3), 97.36 (CAr), 122.80 (CAr), 123.19 (CAr), 125.17 (CAr), 127.26 (CAr), 127.29 (CAr), 127.70 (CAr), 129.33 (CAr), 130.25 (Cq), 130.64 (Cq), 134.79 (CAr), 163.55 (CH) ppm.

GC-MS: (El, 70eV): m/z=286 (M+).

UV (λmax, CH2Cl2): 360 nm (c=1.48×10−5, A=1.20, ε=8.1×104).

Example 4

3-methyl-N-(2-pyrenylmethylen)-5-isoxazolamine

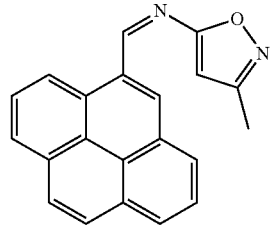 [SMILES: Cc1cc(/N=C\c2cc3cccc4ccc5cccc2c5c43)on1]

5-amino-3-methylisoxazole and 2-pyrenylaldehyde in a molar ratio 1/1 are dissolved in absolute ethanol in the presence of catalytic amount of TsOH and sonicated in an ultrasonic bath. After addition of silica the reaction mixture is irradiated with 360 W microwave radiation for 5 min. The residue is washed with chloroform and dichloromethane. The liquid phase is evaporated and purified by column chromatography using silica gel as solid phase and 1/5=ethyl acetate/n-hexane as the eluent system to yield the compound of the title as yellow crystals (36% yield).

Figure 17:
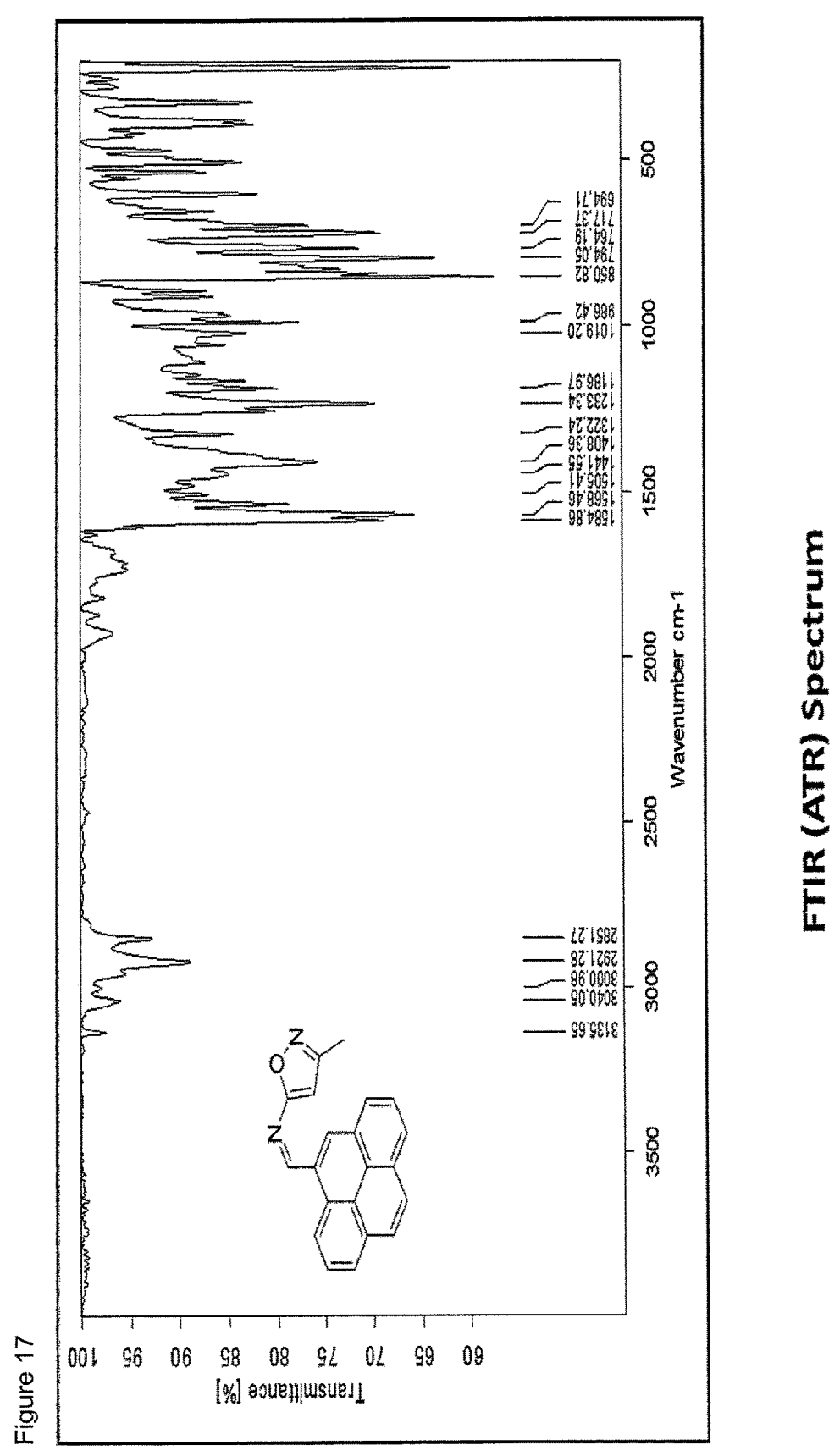
Figure 18:
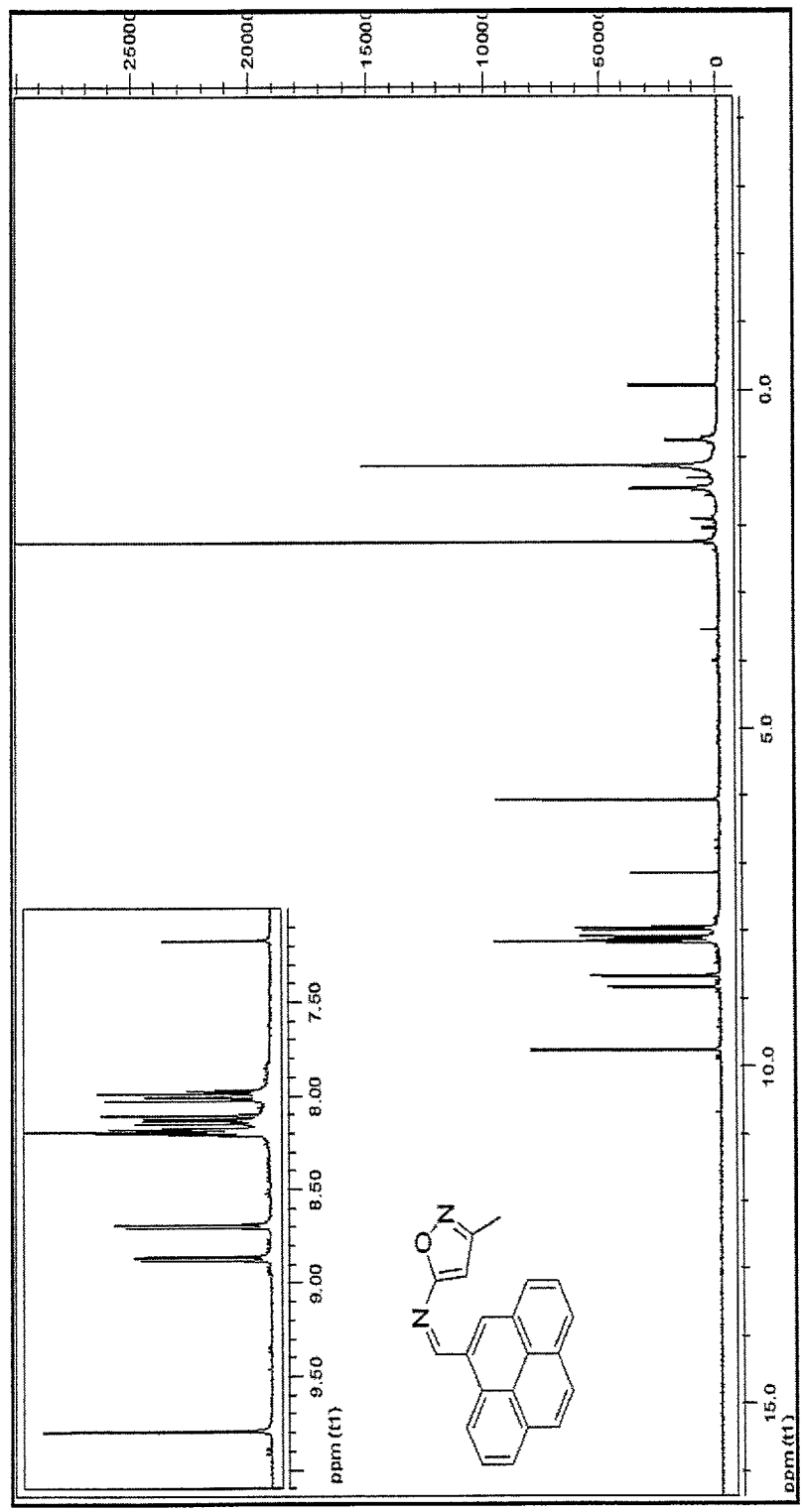
Figure 19:
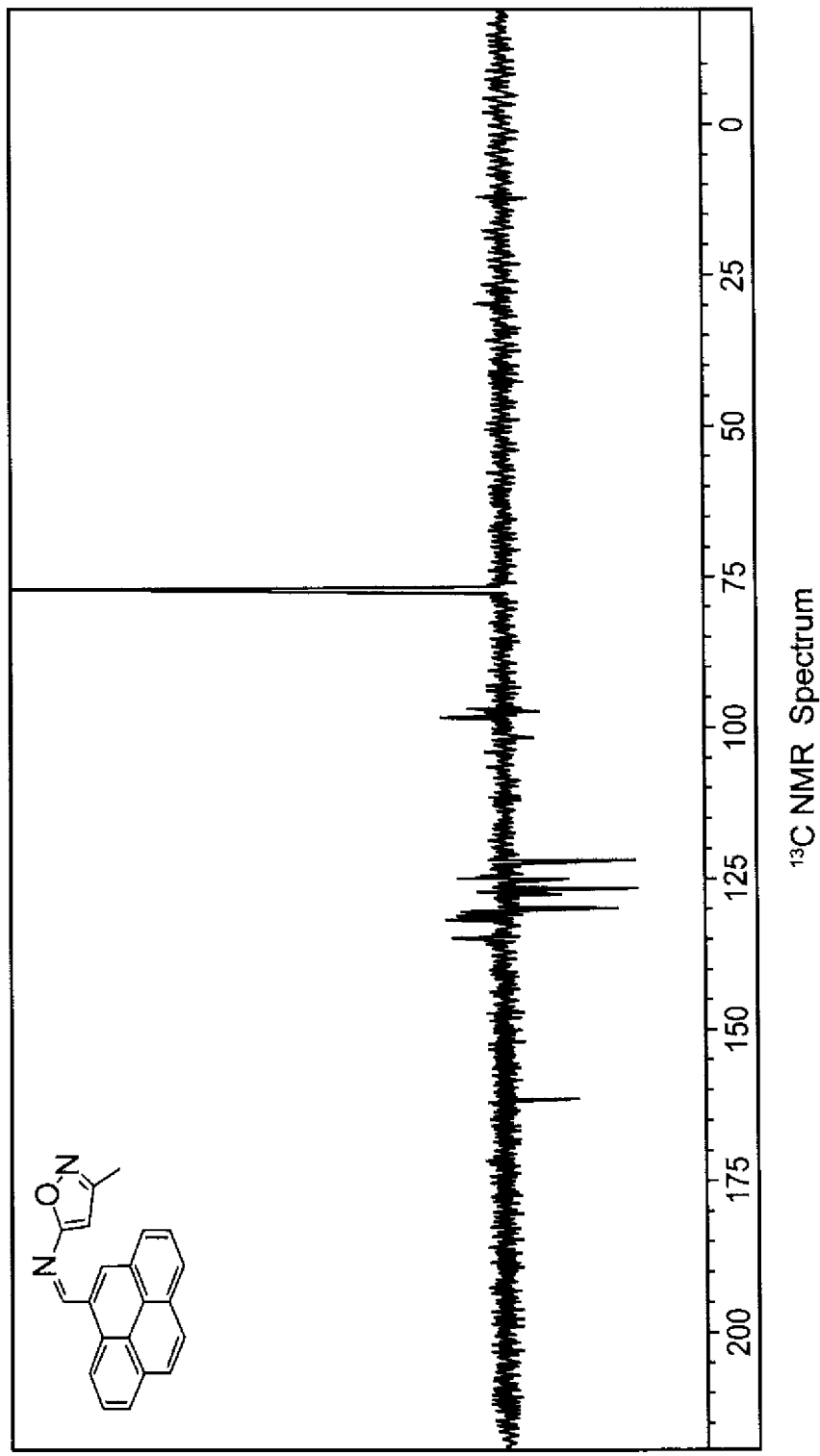
Figure 20:
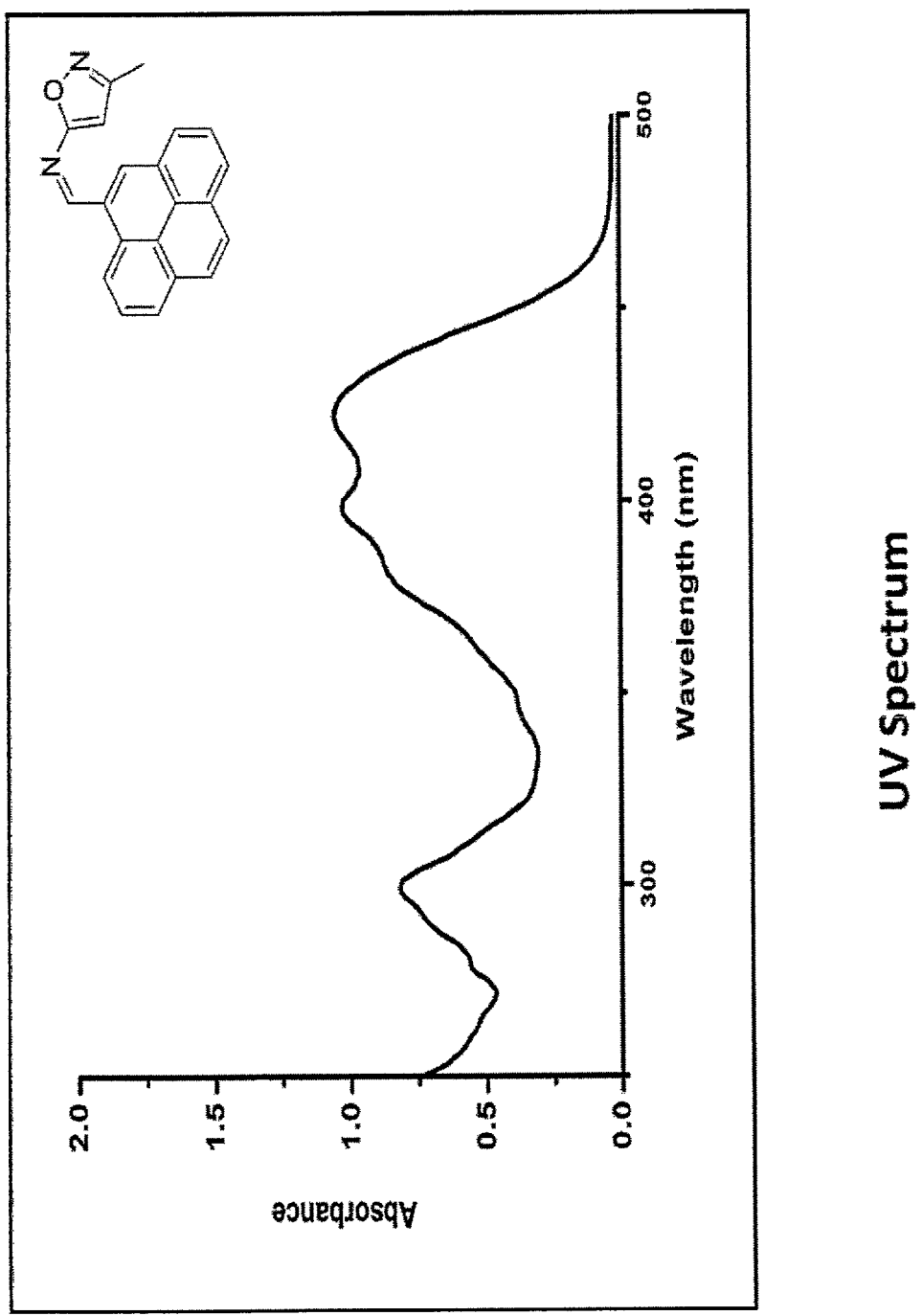

See FIGS. 17 to 20.

m.p.=159-162° C.; $R_f$=0.30 (1:5, ethyl acetate/n-hexane);

FTIR (ATR): ☐=3040 (aromatic, =CH streching), 2921 ve 2851 (aliphatic, CH streching), 1584, 1568 and 1505 (C=C and C=N streching), 1441, 1408 (aliphatic, intraplanar CH bending), 1322 (methyl, intraplanar CH bending), 1186 (C—N swing), 717 ve 694 (monosubstitued aromatic ring, CH bending) cm$^{-1}$.

$^1$H NMR (CDCl3, 500 MHz): δ=2.31 (s, 3H, CH3), 6.11 (s, 1H, =CH), 8.01 (dd, J=7.56; 9.77 Hz, 2H, aromatic), 8.13 (dd, J=8.19; 12.29 Hz, 2H, aromatic), 8.19-8.22 (m, 3H, aromatic), 8.70 (d, J=8.19 Hz, 1H, aromatic), 8.88 (d, J=9.77 Hz, 1H, aromatic), 9.80 (s, 1H, =CH) ppm.

$^{13}$C NMR (CDCl3, 125 MHz): δ=12.12 (CH3), 96.84 (Cq), 97.28 (CAr), 98.32 (Cq), 122.01(CAr), 124.44 (Cq), 124.89 (Cq), 126.40 (CAr), 126.61 (CAr), 126.82 (CAr), 126.96 (CAr), 127.37 (CAr), 129.77 (CAr), 129.87 (CAr), 130.05 (CAr), 130.48 (Cq), 131.18 (Cq), 131.79 (Cq), 134.71 (Cq), 161.40 (CH), 161.89 (Cq) ppm.

UV (λmax, CH2Cl2): 425 nm (c=7.78×10−6, A=1.1, ε=1.8×104).

Example 5

UPF Test
AATCC 183—2004 Method

The transmission of ultraviolet radiation (UV-R) through a specimen is measured on a spectrophotometer at known wavelength intervals.

The ultraviolet protection factor (UPF) is computed as the ratio of the erythemally weighted ultraviolet radiation (UV-R) irradiance at the detector with no specimen to the erythemally weighted UV-R irradiance at the detector with a specimen present.

The erythemally weighted UV-R irradiance at the detector with no specimen present is equal to the summation between wavelength intervals of the measured spectral irradiance times the relative spectral effectiveness for the relevant erythemal action spectra times the UV-R weighting function of the appropriate solar radiation spectrum times the appropriate wavelength interval.

The erythemally weighted UV-R irradiance at the detector with a specimen present is equal to the summation between wavelength intervals of the measured spectral irradiance times the relative spectral effectiveness for the relevant erythemal action spectrum times the spectral transmittance for the specimen times the wavelength interval.

The percent blocking of UVA and UVB radiation is also calculated as disclosed in AATCC 183—2004.

Results

Transmittance or Blocking of Erythemally Weighted Ultraviolet Radiation through Fabrics AATCC 183:2014
Conditioning
Prior to testing: 21±1° C. temperature and 65±2% relative humidity
At time of testing: 21° C. temperature and 66% relative humidity
Ultraviolet protection value for label (According to ASTM D 6603—Unprepared Specimen): 1324
Protection Classification: Excellent UV-protection category to UPF Value 40 or greater.

The results are reported in the Figures, wherein
FIG. 21 shows the results on a sample of a non treated ecru woven fabric.
FIG. 22 shows the results on a sample of a yellow printed woven panel treated with the compound of Example 1;
FIG. 23 shows the results on sample of a light yellow woven swatch-treated with the compound of Example 2;
FIG. 24 shows the results on white woven panel treated with the compound of Example 3;
FIG. 25 shows the results on yellow printed woven panel treated with the compound of Example 4.

As it can be seen from the data reported in the enclosed Figures, all the treated samples showed excellent UV-protection, while the non-treated sample did not.

Example 6

Antimicrobial Test

Antibacterial tests were carried out using Washing Standart: BS EN ISO 6330 5A, and Antibacterial Test Standard: AATCC 147:2011.

The results are reported herein below.

| Inhibition zone mm mean value | Bacteria Growth | Assessment |
|---|---|---|
| >1 | | |
| 0-1 | None | Good effect |
| 0 | | |
| 0 | Slight | Limit of Efficacy |
| 0 | Moderate heavy | Insufficient effect |
| 0 | | |

Test on a Sample of a Yellow Printed Woven Fabric Treated with the Compound of Example 1

| Inhibition Zone mm$^{(1)}$ | Bacteria Growth$^{(2)}$ |
|---|---|
| 0 | (—) |

(—) no bacterial colonies directly under the treated sample in the contact area were observed.
Inhibition zone exists - Good Effect
Width of clear zone of inhibition in mm
(—) no bacterial colonies directly under the treated sample

| Microorganism | Staphylococcus aureus ATCC 6538 Gram (+) |
|---|---|
| Size of sample | 25 × 50 mm |
| Incubation Temperature | 37° C. ± 2° C. |
| Incubation time | 18-24 hrs |
| Number of washing | — |
| Washing method | — |

Test on a Sample of a Light Yellow Printed Woven Fabric Treated with the Compound of Example 2

| Inhibition Zone mm$^{(1)}$ | Bacteria Growth$^{(2)}$ |
|---|---|
| 0 | (—) |

(—) no bacterial colonies directly under the treated sample in the contact area were observed.
Inhibition zone exists - Good Effect
Width of clear zone of inhibition in mm
(—) no bacterial colonies directly under the treated sample

| Microorganism | Staphylococcus aureus ATCC 6538 Gram (+) |
|---|---|
| Size of sample | 25 × 50 mm |
| Incubation Temperature | 37° C. ± 2° C. |
| Incubation time | 18-24 hrs |
| Number of washing | — |
| Washing method | — |

Test on a Sample of a Pink Woven Fabric Treated with the Compound of Example 3

| Inhibition Zone mm$^{(1)}$ | Bacteria Growth$^{(2)}$ |
|---|---|
| 0 | (—) |

(—) no bacterial colonies directly under the treated sample in the contact area were observed.
Inhibition zone exists - Good Effect
Width of clear zone of inhibition in mm
(—) no bacterial colonies directly under the treated sample

| Microorganism | Staphylococcus aureus ATCC 6538 Gram (+) |
|---|---|
| Size of sample | 25 × 50 mm |
| Incubation Temperature | 37° C. ± 2° C. |
| Incubation time | 18-24 hrs |
| Number of washing | — |
| Washing method | — |

Test on a Sample of Yellow Printed Woven Fabric Treated with the Compound of Example 4

| Inhibition Zone mm$^{(1)}$ | Bacteria Growth$^{(2)}$ |
|---|---|
| 0 | (—) |

(—) no bacterial colonies directly under the treated sample in the contact area were observed.
Inhibition zone exists - Good Effect
$^{(1)}$Width of clear zone of inhibition in mm
$^{(2)}$(—) no bacterial colonies directly under the treated sample

| | Staphylococcus aureus ATCC 6538 |
| Microorganism | Gram (+) |
| --- | --- |
| Size of sample | 25 × 50 mm |
| Incubation Temperature | 37° C. ± 2° C. |
| Incubation time | 18-24 hrs |
| Number of washing | — |
| Washing method | — |

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A compound of formula (I):

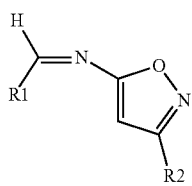

(I)

wherein
R1 is a non-substituted aromatic fused polycyclic hydrocarbon having 10 to 18 carbon atoms and;
R2 is a non-substituted, saturated or unsaturated, linear or branched, acyclic C1-C10 group.

2. The compound according to claim 1, wherein said $R_1$ is selected from the group consisting of naphthalenyl, anthracenyl and pyrenyl groups.

3. The compound according to claim 1, wherein said $R_1$ is a group selected from the group consisting of 1-naphthalenyl; 2-naphthalenyl; 9-anthracenyl and 1-pyrenyl groups.

4. The compound according to claim 1, wherein said $R_2$ is a C1-C4 alkyl group.

5. The compound according to claim 4, wherein said $R_2$ is a methyl group.

6. The compound according to claim 1 wherein said compound is selected from the group consisting of 3-methyl-N-(1-naphthalenylmethylen)-5-isoxazolamine, 3-methyl-N-(2-naphthalenylmethylen)-5-isoxazolamine, 3-methyl-N-(9-phenanthrenylmethylen)-5-isoxazolamine and 3-methyl-N-(2-pyrenylmethylen)-5-isoxazolamine.

7. A method to make fabrics sun-protective and anti-infective, comprising treating said fabrics with at least one compound according to claim 1.

8. A clothing or personal protective equipment (PPE) comprising a fabric treated with at least a compound of claim 1.

9. A process for the preparation of a compound according to claim 1, said process comprising reacting compounds of formula (II) and (III) according to the following scheme

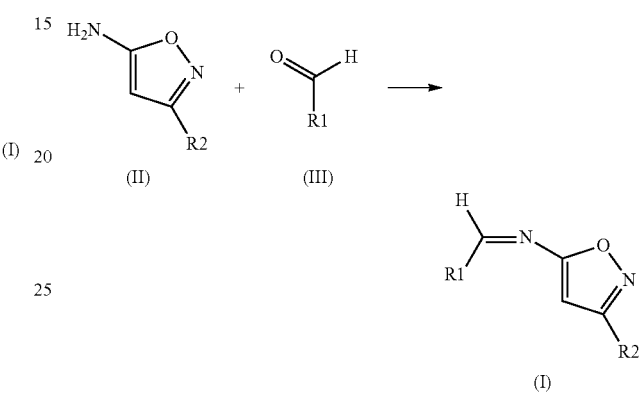

in an appropriate solvent with an acidic catalyst.

10. The process of claim 9, wherein a molar ratio of compound (II)/compound (III) is 1/1.

11. The process of claim 9, wherein said solvent is toluene or ethanol.

12. The process of claim 9, wherein said acidic catalyst is p-toluenesulfonic acid (TsOH).

13. The process of claim 9, wherein said reacting further includes reacting in one or more absorbent agents.

14. The method of claim 7, wherein said fabrics are cotton fabrics.

15. The method of claim 7, wherein said fabrics are denim.

* * * * *